United States Patent
Feldman et al.

(10) Patent No.: US 9,238,830 B2
(45) Date of Patent: Jan. 19, 2016

(54) METHODS AND SYSTEMS FOR O-GLYCOSYLATING PROTEINS

(75) Inventors: Mario Feldman, Edmonton (CA); Amirreza Faridmoayer, Zurich (CH)

(73) Assignee: THE GOVERNORS OF THE UNIVERSITY OF ALBERTA, Edmonton, Alberta (CA)

( * ) Notice: Subject to any disclaimer, the term of this patent is extended or adjusted under 35 U.S.C. 154(b) by 1478 days.

(21) Appl. No.: 12/519,085

(22) PCT Filed: Dec. 13, 2007

(86) PCT No.: PCT/IB2007/004486
§ 371 (c)(1),
(2), (4) Date: Oct. 22, 2009

(87) PCT Pub. No.: WO2008/093165
PCT Pub. Date: Aug. 7, 2008

(65) Prior Publication Data
US 2011/0243980 A1    Oct. 6, 2011

Related U.S. Application Data

(60) Provisional application No. 60/872,403, filed on Dec. 13, 2006.

(51) Int. Cl.
*C12P 21/06*    (2006.01)
*C12P 21/00*    (2006.01)
*C07K 14/22*    (2006.01)

(52) U.S. Cl.
CPC .............. *C12P 21/005* (2013.01); *C07K 14/22* (2013.01)

(58) Field of Classification Search
None
See application file for complete search history.

(56) References Cited

U.S. PATENT DOCUMENTS 6,872,398 B2    3/2005  Castric et al.

OTHER PUBLICATIONS

Chothia et al (The EMBO Journal, 1986, 5/4:823-26).*
Mikayama et al. (Nov.1993. Proc.Natl.Acad.Sci. USA, vol. 90 : 10056-10060).*
Rudinger et al. (Jun. 1976. Peptide Hormones. Biol.Council. pp. 5-7).*
Aas, Finn Erik et al., "*Neisseria gonorrhoeae* O-linked pilin glycosylation: functional analyses define both the biosynthetic pathway and glycan structure," *Molecular Microbiology*, vol. 65(3):607-624 (2007).
Castric, Peter et al., "Structural characterization of the *Pseudomonas aeruginosa* 1244 pilin glycan," *The Journal of Biological Chemistry*, vol. 276(28):26479-26485 (2001).
Faridmoayer, Amirreza et al., "Functional Characterization of Bacterial Oligosaccharyltransferases Involved in O-linked Protein Glycosylation," *Journal of Bacteriology*, vol. 187:1-31 (2007).
Power, Peter M. et al., "Pilin glycosylation in *Neisseria meningitidis* occurs by a similar pathway to *wzy*-dependent O-antigen biosynthesis in *Escherichia coli*," *Biochemical and Biophysical Research Communications*, vol. 347:904-908 (2006).
International Search Report for Application No. PCT/IB2007/004486, dated Apr. 21, 2009.
Office Action from AU 2007345975, dated Jul. 2, 2012.
Supplemental Europan Search Report from EP 07872469.7, dated Apr. 18, 2012.

* cited by examiner

*Primary Examiner* — Jennifer Graser
(74) *Attorney, Agent, or Firm* — Lathrop & Gage LLP; James H. Velema, Esq.

(57) ABSTRACT

Described herein are methods and systems for O-glycosylating proteins in vivo or in vitro in any prokaryotic organism. In these methods and systems, DNA comprising a gene that produces a PglL-like oligosaccharyltransferase and DNA comprising a gene that produces a protein to be O-glycosylated are used. The PglL-like oligosaccharyltransferase facilitates the covalent attachment of the glycan to the protein to produce the O-glycosylated protein. The methods and systems described herein provide an approach for the design and production of new vaccines and therapeutic agents for the treatment of various diseases.

64 Claims, 8 Drawing Sheets

A

*C. jejuni* N-glycan

B

*N. meningitidis*
Gal(ß1-4)Gal(α1-3)DATDH

C

*E. coli* O7

D

*P. aeruginosa* O11

E

*S. enterica* LT2

SEQUENCE LISTING

<160> NUMBER OF SEQ ID NOS: 7

<210> SEQ ID NO 1
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 1
aaagaattca tgaacaccct tcaaaaaggt tttaccctta tcgagc        46

<210> SEQ ID NO 2
<211> LENGTH: 44
<212> TYPE: DNA

```
<213> ORGANISM: Artificial Sequence
<220> FEATURE:
<223> OTHER INFORMATION: Synthetic oligonucleotide

<400> SEQUENCE: 2
tttaagcttt tagctggcat cacttgcgtc gcggcaggtt gacg              44

<210> SEQ ID NO 3
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 3
aaagaattca tgcccgctga aacgaccgta tccggcgcgc                   40

<210> SEQ ID NO 4
<211> LENGTH: 73
<212> TYPE: DNA
<213> ORGANISM: Artificial Sequence
<220> FEATURE:
<223> OTHER INFORMATION: Synthetic oligonucleotide

<400> SEQUENCE: 4
tttaagcttt cagtggtggt ggtggtggtg gtggtggtgg tgtttgcagg gttttgcttc   60
cggatgaccg ggc                                                     73

<210> SEQ ID NO 5
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 5
aatccagtcg acttagtggt ggtggtggtg gtggctggca tcacttgcgt cgcggcaggt   60
tgacg                                                              65

<210> SEQ ID NO 6
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 6
aatccagtcg actcatttgc agggttttgc ttccggatga ccgggc                  46

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Ser Ala Gly Val Ala
1               5
```

METHODS AND SYSTEMS FOR O-GLYCOSYLATING PROTEINS

CROSS REFERENCE TO RELATED APPLICATION

This application claims priority upon U.S. provisional application Ser. No. 60/872,403, filed Dec. 13, 2006. This application is hereby incorporated by reference in its entirety for all of its teachings.

FIELD OF THE INVENTION

The present invention relates to the field of protein glycosylation, and more specifically, to methods and systems for O-glycosylating proteins in prokaryotic organisms.

BACKGROUND

Protein glycosylation is a fundamental process in living organisms. Analysis of the frequency of glycosylation has predicted that more than half of all proteins in nature will eventually be identified as glycoproteins. Without these added carbohydrates, the function of many proteins is aberrant. Complex carbohydrates are involved in cellular communication via cell/cell contact, metastasis (the spread of cancer cells through the body), viral and bacterial adhesion, and binding of toxins to cells. Understanding the roles of carbohydrate biology is crucial to basic health research and to the pharmaceutical industry.

Recombinant glycoproteins represent a major fraction of the active compounds in today's biotech drugs. Examples of therapeutic glycoproteins are recombinant human Erythropoietin (rHuEPO), beta-Interferon, and Follicle stimulating hormone (FSH). While the biological function is typically determined by the protein component, carbohydrates can affect many properties of the protein, which can include, but are not limited to, molecular stability, serum half-life, solubility, in vivo activity, and immunogenicity. For example, hHuEPO, which can be produced in Chinese hamster ovary cells, is used clinically to treat numerous anemias including, but not limited to, those associated with chronic renal failure, HIV infection and some types of cancers. rHuEPO contains several oligosaccharide chains containing sialic acid as the terminal sugar. Removal of the sialic acid residues from rHuEPO results in virtually inactive rHuEPO in vivo due to its rapid clearance. This example shows the importance of a defined carbohydrate structure and pattern for the biological activity of recombinant glycoproteins.

In the past, mammalian, insect, and yeast cells have been used to express recombinant glycoproteins. These cells all have the capability to glycosylate proteins, but they exhibit different patterns of glycosylation than human cells. Because protein glycosylation is an essential process in eukaryotic cells and very complex sugar modifications occur in the different cellular compartments, the manipulation of protein glycosylation in higher organisms is very difficult. Consequently, the use of these types of cells often results in the production of glycoproteins having different carbohydrate structures and patterns, which may lead to serious changes in properties, as described above. These different carbohydrate structures and patterns may in fact lead to the production of recombinant glycoproteins that are completely inactive and useless for the production of therapeutic agents. Consequently, there is a need for methods and systems that can be used to produce recombinant glycoproteins having specific carbohydrate structures and patterns both in vivo and in vitro.

Until recently, glycoproteins were thought to be an exclusive feature of eukaryotic cells. Although protein glycosylation does not take place naturally in *Escherichia coli*, it is a common phenomenon in other bacteria. Bacteria can tolerate the manipulation of their glycosylation systems and therefore constitute perfect toolboxes for glycoengineering.

Protein glycosylation consists of two main steps: (i) the assembly of a glycan and (ii) the attachment of the glycan to the protein. In most cases, the glycans are sequentially assembled onto a lipid carrier by different glycosyltransferases. This lipid carrier will vary depending on the organism. For example, which is not meant to be limiting, the lipid carrier can be dolichol-pyrophosphate in the membrane of the endoplasmic reticulum of eukaryotic cells and can be undecaprenol-pyrophosphate (Und-PP) in the inner membrane of bacteria. Once the glycans are assembled onto the lipid carrier, they are transferred to target proteins. When the glycans are attached to the amido groups of selected asparagine (Asn) residues, the process is called N-glycosylation. During the process of O-glycosylation, glycans are attached to the hydroxyl group on selected serine (Ser) or threonine (Thr) residues. The transfer of the glycans from the lipid carrier to proteins is carried out by enzymes named oligosaccharyltransferases (OTases).

In conjugate vaccine production, glycoproteins are used as vaccines to help elicit an immune response and provide protection against various pathogens and other ailments. In these vaccines, the attachment of glycans to proteins helps increase the immunogenecity of the glycans. Many techniques are now available to produce such vaccines (Jones, C. 2005 *An. Acad. Bras. Cienc.* 77(2): 293-324; Sood, R. K., and Fattom, A. 1998 *Expert Opin. Investig. Drugs* 7(3):333-347; Slovin, S. F., Keding, S. J., Ragupathi, G. 2005 *Immunol. Cell Biol.* 83(4):418-428). However, when using most of the currently available techniques, it is not possible to control the site(s) on the protein where the glycan will be attached. Furthermore, it can be quite difficult the control the ratio of glycan to protein. These difficulties lead to conjugate vaccines that are heterogeneous in nature, which leads to problems when trying to gain approval for use from health regulatory agencies. The composition of the conjugate vaccines may vary and are often hard to reproduce exactly. Consequently, there is a need for new methods and systems that can be used to attach glycans to proteins in a more controlled manner to improve the production of conjugate vaccines.

The use of bacteria to produce O-glycosylated recombinant proteins has been disclosed by Castric et al. in U.S. Pat. No. 6,872,398 (the "'398 Patent"). In the '398 Patent, a multivalent vaccine against Gram-negative bacterial infections comprising heterologously glycosylated pili from *Pseudomonas aeruginosa* is disclosed. To produce this vaccine, the '398 Patent teaches the introduction into a Gram-negative bacterium, of a vector containing pilA, the pilin structural gene from *Pseudomonas aeruginosa*, and pilO, the gene from *Pseudomonas aeruginosa* coding for the protein responsible for the attachment of the O-antigen repeating unit to the pilin subunit. Once expressed, PilO can add the O-antigen repeating unit of the host Gram-negative bacterium to the pilin protein PilA. The O-glycosylated pilin can then be purified from a culture of the transformed bacteria. However, this method and system have many serious disadvantages and limitations. The system taught by Castric relies strictly on the use of the oligosaccharyltransferase PilO. This limitation results in several serious disadvantages. First, the use of PilO severely limits the type of O-antigen repeating units that can be transferred onto the glycoprotein. In fact, PilO can only transfer only small glycans, commonly known by one of skill in the art as oligosaccharides (i.e., glycans having 2-10 monosaccharides). Second, PilO is unable to transfer glycans to internal glycosylation sites in proteins to be glycosylated. In fact, it has been shown that PilO only transfers glycan to a serine residue that must be the C-terminal residue of the protein (Castric, P., et al. 2001, *J. Biol. Chem.* 276;26479-26485). This clearly imposes major limits on the proteins that can be glycosylated using the system taught by Castric. Moreover, these difficulties can prevent the production of specific vaccines or therapeutic agents due to PilO's inability to transfer larger glycan, commonly known by one of skill in the art as polysaccharides (i.e., glycans having more than 10 monosaccharides). Third, PilO is very difficult to express and purify. This can pose serious limitations when trying to use this system to produce large quantities of glycosylated product for vaccine production.

The system and method taught by Castric in U.S. Pat. No. 6,872,398 have several other limitations. The production of recombinant glycoproteins is limited to in vivo systems. Moreover, both the oligosaccharyltransferase and the protein to be glycosylated must originate from *Pseudomonas aeruginosa*. These disadvantages can be very problematic, mostly for the production of vaccines or other therapeutic agents.

Consequently, the need has arisen for a method and system that can be used to easily O-glycosylate proteins using a variety of prokaryotic organisms in an in vivo or in vitro manner, while avoiding some of the problems listed above.

SUMMARY

In accordance with a broad aspect of the invention, there is provided a method for O-glycosylating proteins with a glycan in a prokaryotic organism. The method comprises introducing into the prokaryotic organism, in any particular order, at least (a) DNA comprising a gene that produces a PglL-like oligosaccharyltransferase, and DNA comprising a gene that produces a protein to be O-glycosylated. The PglL-like oligosaccharyltransferase facilitates the covalent attachment of the glycan to the protein to produce the O-glycosylated protein. The glycan comprises monosaccharides, oligosaccharides, polysaccharides, or any combination thereof. In one aspect, the glycan comprises a hexose or an N-acetyl hexose derivative at the reducing end. In another aspect, galactose is present at the reducing end of the glycan. The lipid carrier is a polyprenol-pyrophosphate including, but not limited to, undecaprenol-pyrophosphate, dolichol-pyrophosphate, and synthetic equivalents thereof.

In accordance with another broad aspect of the invention, there is provided a method for producing O-glycosylating proteins with a glycan in a prokaryotic organism, where the method comprises introducing into the prokaryotic organism, in any particular order, at least (a) DNA comprising pglL that produces a PglL-like oligosaccharyltransferase, (b) DNA comprising pilE that produces a protein to be O-glycosylated; and (c) DNA comprising genes required for the assembly of a glycan onto a lipid carrier. The PglL-like oligosaccharyltransferase facilitates the covalent attachment of the glycan to the protein to produce the O-glycosylated proteins. The glycan comprises monosaccharides, oligosaccharides, polysaccharides or any combination thereof. In one aspect, the glycan comprises a hexose or an N-acetyl hexose derivative at the reducing end. In another aspect, galactose is present at the reducing end of the glycan. The lipid carrier is a polyprenol-pyrophosphate including, but not limited to, undecaprenol-pyrophosphate, dolichol-pyrophosphate, and synthetic equivalents thereof.

In accordance with another broad aspect of the invention, there is provided a system for producing an O-glycosylated protein comprising a prokaryotic organism and at least the following components present within the organism: (a) DNA that produces a PglL-like oligosaccharyltransferase; (b) DNA that produces the protein to be O-glycosylated; and (c) DNA comprising genes required for the assembly of a glycan onto a lipid carrier. The PglL-like oligosaccharyltransferase facilitates the covalent attachment of the glycan to the protein to produce the O-glycosylated protein. The glycan comprises monosaccharides, oligosaccharides, polysaccharides, or any combination thereof. In one aspect, the glycan comprises a hexose or an N-acetyl hexose derivative at the reducing end. In another aspect, galactose is present at the reducing end of the glycan. The lipid carrier is a polyprenol-pyrophosphate including, but not limited to, undecaprenol-pyrophosphate, dolichol-pyrophosphate, and synthetic equivalents thereof.

In accordance with another broad aspect of the invention, there is provided a system for producing an O-glycosylated protein comprising a prokaryotic organism and at least the following components present within the organism: (a) DNA comprising pglL that produces a PglL-like oligosaccharyltransferase; (b) DNA comprising pilE that produces the protein to be O-glycosylated; and (c) DNA comprising genes required for the assembly of a glycan onto a lipid carrier. The oligosaccharyltransferase facilitates the covalent attachment of the glycan to the protein to produce the O-glycosylated protein. The glycan comprises monosaccharides, oligosaccharides, polysaccharides, or any combination thereof. In one aspect, the glycan comprises a hexose or an N-acetyl hexose derivative at the reducing end. In another aspect, galactose is present at the reducing end of the glycan. The lipid carrier is a polyprenol-pyrophosphate includes, but is not limited to, undecaprenol-pyrophosphate, dolichol-pyrophosphate, and synthetic equivalents thereof.

In accordance with another broad aspect of the invention, there is provided a method for producing an O-glycosylated protein comprising reacting: (a) the protein to be O-glycosylated, and (b) a glycan bound to a lipid carrier in the presence of a PglL-like oligosaccharyltransferase. The PglL-like oligosaccharyltransferase transfers the glycan from the lipid carrier to the protein. The glycan comprises monosaccharides, oligosaccharides, polysaccharides, or any combination thereof. In one aspect, the glycan comprises a hexose or an N-acetyl hexose derivative at the reducing end. In another aspect, galactose is present at the reducing end of the glycan. The lipid carrier is a polyprenol-pyrophosphate includes, but is not limited to, undecaprenol-pyrophosphate, dolichol-pyrophosphate, and synthetic equivalents thereof.

In accordance with another broad aspect of the invention, there is provided a method for producing an O-glycosylated protein comprising reacting (a) PilE protein that is the expression product of pilE, and (b) a glycan bound to a lipid carrier in the presence of an oligosaccharyltransferase that is the expression product of pglL. The oligosaccharyltransferase transfers the glycan from the lipid carrier to the protein. The glycan comprises monosaccharides, oligosaccharides, polysaccharides, or any combination thereof. In one aspect, the glycan comprises a hexose or an N-acetyl hexose derivative at the reducing end. In another aspect, galactose is present at the reducing end of the glycan. The lipid carrier is a polyprenol-pyrophosphate includes, but is not limited to, undecaprenol-pyrophosphate, dolichol-pyrophosphate, and synthetic equivalents thereof.

In accordance with another broad aspect of the invention, there is provided an O-glycosylated protein produced by the methods and systems described herein that can be used for the production of a vaccine. These methods and systems are particularly advantageous since they can be used to prepare O-glycosylated proteins without introducing limitations as to the type of glycan that can be added to proteins, the length of the glycan transferred, the type of sugar located at the reducing end of the glycan, the position of the glycan on the protein or the type of organisms that can be used.

BRIEF DESCRIPTION OF THE DRAWINGS

The present invention, both as to its organization and manner of operation, may best be understood by reference to the following description, and the accompanying drawings of various embodiments wherein like numerals are used throughout the several views, and in which.

DETAILED DESCRIPTION OF THE INVENTION

Figure 1:
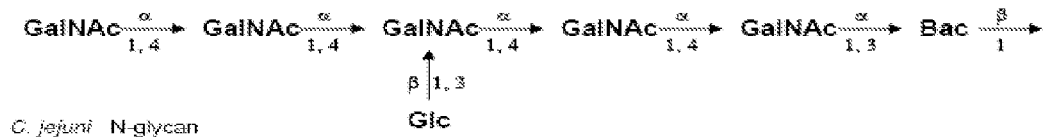
FIG. 1A is a schematic diagram of the N-glycan produced by C. jejuni.
FIG. 1B is a schematic diagram of the pilin glycan produced by N. meningitidis.
FIG. 1C is a schematic diagram of the O7 antigen produced by E. coli.
FIG. 1D is a schematic diagram of the pilin glycan produced by P. aeruginosa O11.
FIG. 1E is a schematic diagram of glycan produced by S. enterica serovar Typhimurium.
Figure 1:
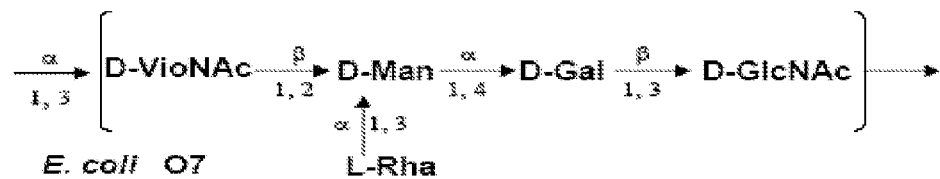
Figure 1:
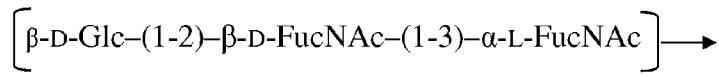
Figure 1:
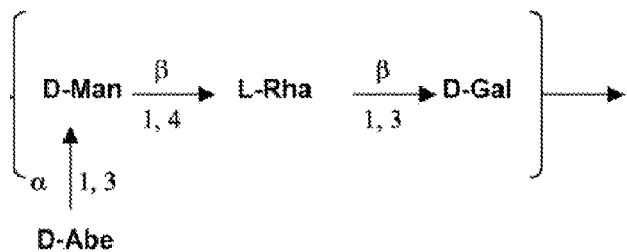

The materials, compounds, compositions, and methods described herein may be understood more readily by reference to the following detailed description of specific aspects of the disclosed subject matter and the Examples included therein and to the Figures.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "an agent" includes mixtures of two or more such agents.

The present invention relates to the discovery of methods and systems for O-glycosylating proteins in vivo or in vitro. In vivo methods and systems comprise introducing into any prokaryotic organism, in any particular order, at least: (i) DNA that produces a PglL-like oligosaccharyltransferase, and (ii) DNA that produces a protein to be O-glycosylated. In one embodiment, these methods and systems rely on genes that code for proteins required for the assembly of a glycan onto a lipid carrier, which are endogenous to the prokaryotic organism and are required for glycosylation. In another embodiment, these methods and systems further comprise introducing into the prokaryotic organism exogenous genes coding for proteins that are required for the assembly of a glycan onto a lipid carrier. These methods and systems are particularly advantageous since they can be used to prepare O-glycosylated proteins without introducing limitations as to the type of glycan that can be added to proteins, the length of the glycan transferred, the type of sugar located at the reducing end of the glycan, the position of the glycan on the protein or the type of organisms that can be used.

In vitro methods and systems comprise incubating a PglL-like oligosaccharyltransferase with a protein to be O-glycosylated and with a lipid-linked glycan in a suitable buffer.

For the purposes of this invention, a glycan comprises any sugar that can be transferred (e.g, covalently attached) to a protein. A glycan comprises monosaccharides, oligosaccharides and polysaccharides. As described above, an oligosaccharide is a glycan having 2 to 10 monosaccharides. A polysaccharide is a glycan having greater than 10 monosaccharides. Polysaccharides can be selected from the group comprising O-antigens, capsules, and exopolysaccharides. Of course, one of skill in the art will appreciate that other types of polysaccharides may also be used.

Glycans useful herein include, but are not limited to, hexoses, N-acetyl derivatives of hexoses, oligosaccharides, and polysaccharides. Other examples, which are not meant to be limiting, include glycans from *C. jejuni, N. meningitidis, P. aeruginosa, S. enterica* LT2, and *E. coli* (see FIG. 1). In one embodiment, the monosaccharide at the reducing end of the glycan is a hexose or an N-acetyl derivative of a hexose. In one aspect, the hexose can be galactose. In one aspect, the N-acetyl derivative of hexose can be selected from the group comprising N-acetylglucosamine (GlcNAc), 2-Acetamido-2, 6-dideoxyhexose (FucNAc), and DATDH (2,4-diacetarnido-2,4,6-trideoxyhexose).

A PglL-like oligosaccharyltransferase of the present invention includes oligosaccharyltransferases comprising the following properties: (a) ability to transfer glycans to serine or threonine residues of proteins; (b) ability to transfer glycans having different lengths and different types of monosaccharides due to relaxed glycan specificity; and (c) ability to transfer polysaccharides to proteins during O-glycosylation. In one aspect, PglL-like oligosaccharyltransferase can also have the ability to transfer glycans to internal glycosylation sites in proteins to be O-glycosylated. In one aspect, PglL-like oligosaccharyltransferase can also have the ability to O-glycosylate proteins in the periplasm of prokaryotic organisms.

In one embodiment, the PglL-like oligosaccharyltransferase is the protein expressed by pilin-glycosylation gene L (pglL) or a homologue thereof. Of course, one of skill in the art will understand that homologues are proteins that may have differences in sequence, but no major difference in function. In one aspect, proteins expressed by pglL or homologues thereof in *Neisseria* (e.g., *N. meningitidis* or *gonorrhea*) can produce oligosaccharyltransferases useful herein. Examples of genomic sequences of pglL from *N. meningitidis* for the expression of PglL-like oligosaccharyltransferases useful herein include, but are not limited to, PglL from MC58 (Accession No. AAF41024) (Tettelin, H. et al., 2000, *Science* 287:1809-1815), Z7491 (Parkhill, J., et al., 2000, *Nature* 404:502-506), and FAM18 (http://www.sanger.ac.uk/Projects/N_meningitdis/sero.shtml)). PglL from *N. gonorrhea* has been termed PglO (Accession No. NGO0178) (Aas, F. E. et al., 2007, *Mol. Microbiol.* 65:607-624).

In one embodiment of the present invention, O-glycosylated proteins are prepared using in vivo methods and systems. These methods and systems can be used to produce O-glycosylated proteins in any type of prokaryotic organism. The selection of the prokaryotic organism can vary widely. In one embodiment, the prokaryotic organism is a Gram-negative bacterium. Gram-negative bacteria that can be used include, but are not limited to, species of bacteria from the genera *Neisseria, Salmonella, E. coli, Pseudomonas* and *Yersinia*.

In a particular embodiment of the present invention, the prokaryotic organism used is *Escherichia coli*. The use of *E. coli* has many advantages. *E. coli* has been used in the design of vaccines and therapeutic agents, and is a good host cell for conducting in vivo O-glycosylation reactions. Of course, as will be apparent to one of skill in the art, the use of *E. coli* has many other advantages, which are not listed herein.

In another embodiment, the prokaryotic organism used is *Salmonella*. The use of *Salmonella* also has many advantages. For example, which is not meant to be limiting, there are many applications of *Salmonella*, where this species is used to produce attenuated vaccines. Moreover, *Salmonella* invariably produces endogenous glycans having galactose at the reducing end of the glycan. One of skill in the art will appreciate that this would then greatly facilitate the production of vaccines.

The methods for in vivo O-glycosylation of proteins of the present invention generally involve the incorporation of at least: (i) DNA that produces a PglL-like oligosaccharyltransferase, and (ii) DNA that produces a protein to be O-glycosylated. As discussed above, in one embodiment, these methods and systems rely on the prokaryotic organism's endogenous genes that code for proteins required for the assembly of a glycan onto a lipid carrier and are necessary for protein glycosylation. In another embodiment, these methods and systems further comprise introducing into the prokaryotic organism exogenous genes coding for proteins that are required for the assembly of a glycan onto a lipid carrier.

The incorporation of these DNA fragments into a prokaryotic organism can be performed using any number of techniques known in the art. One of skill in the art will appreciate that these techniques include any method that can be used to stably transfect or transform a host cell with any recombinant DNA constructs. For example, which is not meant to be limiting, any of the techniques listed and described in *Molecular Cloning: A Laboratory Manual* (Sambrook, J. and Russell, D. W., CSHL Press, Cold Spring Harbor, N.Y., 3$^{rd}$ Edition, 2001) can be readily used to introduce DNA fragments into a prokaryotic organism for the purposes of this invention.

The DNA fragments inserted into the chosen prokaryotic organism are generally genes or a portion of gene(s), which can include truncations and/or mutations thereof, used to produce a PglL-like oligosaccharyltransferase, a protein to be glycosylated, and, in some embodiments, proteins required for the assembly of a glycan onto a lipid carrier. These DNA fragments can be produced in a wide variety of different ways. Each DNA fragment may be generated in any manner, including, for example, which are not meant to be limiting, chemical synthesis or DNA replication or reverse transcription or transcription, which are based on the information provided by the sequence of bases in the region(s) from which the polynucleotide is derived. Moreover, combinations of different regions corresponding to that of the desired sequence may be modified in ways known in the art to be consistent with the intended use. Finally, the source of each DNA fragment can be derived from the same prokaryotic organism or from different prokaryotic organisms, depending on the intended use.

In one embodiment of the present invention, each DNA fragment relates to a recombinant DNA molecule that includes a vector and the DNA fragment as described above. The vector can take the form of a plasmid such as any broad host range expression vector known in the art. Of course, one of skill in the art will appreciate that, in some cases, it may be beneficial to include more than one of the DNA fragments on a single plasmid, depending on the intended use. Moreover, as discussed above, in some embodiments, some of the required proteins are encoded by genes endogenous to the prokaryotic organism. In these embodiments, the DNA fragments encoding these proteins are located in the prokaryotic organism's genome.

In the methods and systems of the present invention, the PglL-like oligosaccharyltransferase facilitates the covalent attachment of the desired glycan to the hydroxyl group of a serine or threonine residue present in the protein to be glycosylated. The DNA fragment encoding the PglL-like oligosaccharyltransferase can be obtained from a wide variety of different systems and organisms. Of course, as described above, any of these sequences may be modified using any method known in the art for the intended use.

In the methods and systems of the present invention, the protein to be glycosylated can be selected from a wide range of proteins. In one embodiment of the invention, when the PglL-like oligosaccharyltransferase used is made from the gene pglL from *N. meningitidis* MC58 (Accession No. AAF41024), the DNA fragment that produces the protein to be glycosylated contains the gene pilE (Accession No. AAF40497) or a homologue thereof. The gene for pilE or a homologue thereof can be selected from a wide variety of different organisms. In one aspect, the DNA fragment for pilE is selected from *Neisseria* (e.g., *meningitidis* or *gonorrhea*). Of course, as described above, these sequences may be modified using any method known in the art for the intended use. When using the protein expressed by the gene pilE from *N. meningitidis* MC58 (Accession No. AAF40497), Ser63 of the mature protein is glycosylated by the PglL-like oligosacccharyltransferase expressed by the gene pglL from *N. meningitidis* MC58 (Accession No. AAF41024). Of course, as will be appreciated by one of skill in the art, the site of glycosylation may differ depending on which protein is selected.

In another embodiment of the present invention, the protein to be glycosylated may be a modified protein such as a hybrid protein containing the determinants for glycosylation. For the purposes of this invention, while wishing not to be bound by theory, determinants for glycosylation are sites recognized by PglL-like oligosaccharyltransferases as glycosylation sites. For example, which is not meant to be limiting, a hybrid protein may be made using methods known in the art, wherein the resulting protein contains the glycosylation determinants from two different proteins. Of course, one of skill in the art will also appreciate that many other hybrid proteins can be made.

In a further embodiment of the invention, the protein to be glycosylated is not a pilin protein. Any protein comprising the determinants of glycosylation recognized by PglL-like oligosacchryltransferase is meant to be included within the methods and systems of the present invention.

The third DNA fragment used for in vivo glycosylation comprises genes required for the assembly of a glycan onto a lipid carrier. As discussed above, glycans useful herein include, but are not limited to, hexoses, N-acetyl derivatives of hexoses, oligosaccharides, and polysaccharides. In one aspect, when a PglL-like oligosaccharyltransferase is used, it is possible to O-glycosylate proteins with polysaccharides or with glycans having hexoses or N-acetyl derivatives of hexoses at the reducing end, as described above. The O-glycosylation of proteins with polysaccharides or with glycans having hexoses or N-acetyl derivatives of hexoses at the reducing end is very advantageous. For example, which is not meant to be limiting, the ability to produce proteins that are O-glycosylated with such glycans is very useful for the development of vaccines and therapeutic agents, as will be discussed later.

In one embodiment of the invention, a DNA fragment containing the gene(s) that produces glycans from one or more organism can also be used. For example, which is not meant to be limiting, the gene(s) responsible for producing the glycans from C. jejuni, N. meningitidis, P. aeruginosa, and E. coli can be used herein (see FIG. 1). These genes can be further involved in the assembly and translocation of glycans. These genes can include, but are not limited to genes encoding glycosyl transferases and other enzymes required for assembly and transport of glycans.

In certain aspects of the invention, depending upon the selection of the prokaryotic organism, in vivo glycan synthesis may also involve attaching sugar units on a lipid carrier such as a polyprenol-pyrophosphate carrier or synthetic equivalent thereof. For example, which is not meant to be limiting, undecaprenol-pyrophosphate (or undecaprenol-PP) may be selected as the polyprenol-pyrophosphate carrier. Alternatively, it is possible to introduce one or more genes that produce these enzymes. Not wishing to be bound by theory, it is believed that O-glycosylation occurs in the periplasm of the organism (e.g., E. coli). As will be appreciated by one of skill in the art, the introduction of these genes as well as the other DNA fragments described above, allows, for the first time, for the production of O-glycosylated proteins in any prokaryotic organism.

Using the in vivo methods and systems described above, it is possible to produce large-scale amounts of O-glycosylated proteins. Prokaryotic organisms transformed with the DNA fragments described above can be grown using various methods known in the art. For example, which is not meant to be limiting, these prokaryotes can be grown in a broth culture to produce the O-glycosylated protein and the O-glycosylated protein can be isolated. The isolation of the O-glycosylated proteins can be performed using various methods known in the art. For example, which is not meant to be limiting, lectin affinity chromatography may be used (Faridmoayer, A. et al., 2007, J. Bacteriol. 189(22):8088-8098).

Although the methods described above are useful for in vivo production of glycosylated proteins, another embodiment of the present invention provides methods and systems for the in vitro production of O-glycosylated proteins. In one embodiment, the method comprises reacting the PilE protein that is an expression product of pilE (Accession No. AAF40497) with a glycan attached to an undecaprenol-PP carrier, in the presence of a PglL-like oligosaccharyltransferase. In one aspect, the PglL-like oligosaccharyltransferase is PglL expressed from the pglL gene from N. meningitidis MC58 (Accession No. AAF41024).

One of skill in the art will appreciate that the DNA fragments encoding pilE and pglL may be modified or truncated using methods known in the art for the intended use. These DNA fragments can be expressed in an organism as discussed above and both proteins can be purified using techniques known in the art. For example, which is not meant to be limiting, the oligosaccharyltransferase produced from pglL is purified from solubilized membrane fractions using techniques known in the art.

To produce O-glycosylated proteins in vitro, the oligosaccharyltransferase can be incubated with protein and glycan that are expressed by various prokaryotic organisms. Of course, one of skill in the art will appreciate that the protein and glycan do not have to originate from the same prokaryotic organism. As will be appreciated by one of skill in the art, incubation conditions can vary widely. For example, which is not meant to be limiting, the proteins and glycans may be incubated in a buffer having a pH of approximately 6 to approximately 8. In one aspect, the buffer may be phosphate buffer saline. In another aspect, the buffer may be Tris-HCl 50 mM, having a pH of 7.5.

The glycosylated protein can then be purified and characterized by techniques known in the art. For example, which is not meant to be limiting, the techniques disclosed in Kowarik et al. (2006, Science, 314:1148-1150) can be adapted herein for the in vitro production of O-glycosylated proteins.

The glycosylated proteins produced herein can be used as therapeutic agents for the treatment of a number of diseases, where an effective amount of the O-glycosylated protein is administered to a subject in need of such treatment. Examples of these diseases include, but are not limited to, autoimmune disorders, HIV and Hepatitis C infections, tuberculosis, candidiasis, leishmaniasis and various bacterial infections. Moreover, it has been shown that some glycans have potential applications for the treatment of several autoimmune diseases that affect a portion of the human population.

The glycosylated proteins produced herein can also be used as a vaccine or in a pharmaceutical composition for the prevention of a disease when an effective amount of the protein is administered to a subject in need of such treatment. Thus, the methods described herein for producing of a number of different O-glycosylated proteins will prove very useful in drug discovery.

The following MATERIALS AND METHODS were used in the examples that follow. These materials and methods are for illustrative purposes only and are not to be construed as limiting the scope of the invention in any way. One of skill in the art will appreciate that several modifications and substitutions can be made without affecting the scope of the invention. More specifically, these include modifications and substitutions in the specific techniques and reaction conditions listed below.

Bacterial Strains, Plasmids, and Growth Conditions

E. coli and P. aeruginosa 1244 cells can be grown on LB at 37° C. Trimethoprim at 100 µg/mL, tetracycline at 20 µg/mL, spectinomycin at 80 µg/mL, chloramphenicol at 20 µg/mL, kanamycin 50 µg/mL, and ampicillin at 100 µg/mL were added in media when required. E. coli and P. aeruginosa strains as well as DH5α plasmids that can be used are listed in Table 1. Of course, one of skill in the art will appreciate that other strains and plasmids not listed in Table 1 may also be used.

TABLE 1

| Strain | Description | Source/Reference |
|---|---|---|
| *Bacterial strains* | | |
| *E. coli* DH5α | F-φ80lacZΔM15 Δ(lacZYA-argF) U169 deoR recA1 endA1 hsdR17 ($r_k$−, $m_k$+) gal phoA supE44 λ⁻thi⁻1 gyrA96 relA1 | Invitrogen |
| *E. coli* CLM24 | W3110 lacking WaaL ligase | Feldman, M. F. et al., 2005, Proc. Natl. Acad. Sci. U.S.A. 102: 3016-21. |
| *E. coli* Sφ874 | LacZ trp Δ(sbcB-rfb) upp rel rpsL | Neuhard, J., and E. Thomassen. 1976, J. Bacteriol. 126: 999-1001. |
| *E. coli* SCM3 | Sφ874, ΔwaaL | Faridmoayer, A. et al., supra |
| *E. coli* SCM7 | Sφ874, Δwec | Alaimo, C., et al., 2006, Embo J. 25: 967-76. |
| *E. coli* JM109 (P4729) expressing *salmonella* O antigen, SGSC# 2442. | *E. coli* JM109 transformed with pPR1347, encoding *S. enterica* LT2 O antigen, $Km^R$ | *Salmonella* Genetic Stock, University of Calgary (SGSC) |
| *Salmonella enterica* serovar Typhimurium (SL3749), SGSC# 228 | Serogroup B, O antigen ligase mutant (Δrfal) | *Salmonella* Genetic Stock, University of Calgary (SGSC) |
| *Salmonella enterica* serovar Typhimurium (SL901), SGSC# 82 | Serogroup B, O antigen polymerase mutant (Δwzy) | *Salmonella* Genetic Stock, University of Calgary (SGSC) |
| *Salmonella enterica* Typhi | O antigen polymerase mutant (Δwzy) | Hoare, A. et al., 2006, Infect. Immun. 74(3): 1555-64 |
| *Plasmids* | | |
| pSPORT1 | Cloning vector, $Amp^R$ | Invitrogen |
| pMLBAD | Cloning vector, arabinose-inducible, $Tmp^R$ | Lefebre, M. D., and M. A. Valvano. 2002, Appl. Environ. Microbiol. 68: 5956-64. |
| pEXT20 | Cloning vector, IPTG-inducible, $Amp^R$ | Dykxhoorn, D. M., R. St Pierre, and T. Linn. 1996, Gene 177: 133-6 |
| pEXT21 | Cloning vector, IPTG-inducible, $Sp^R$ | |
| pEXT22 | Cloning vector, IPTG-inducible, $Km^R$ | |
| pPAC46 | Encodes *P. aeruginosa* 1244 pilA-pilO operon, $Amp^R$ | Castric, P. 1995. Microbiology 141 (Pt 5): 1247-54. |
| pACYCpgl | Encodes the *C. jejuni* pgl cluster, $Cm^R$ | Wacker, M., et al., supra |
| pACYCpglB$_{mut}$ | Encodes the *C. jejuni* pgl containing mutations W458A and D459A in PglB, $Cm^R$ | |
| pACYCpglKmut | Encodes *C. jejuni* pgl containing a Km cassette in pglK, $Cm^R$, $Km^R$ | Alaimo, C. et al., supra |
| pLPS2 | Encodes the O11 antigen cluster from *P. aeruginosa* PA103, $Tet^R$ | Goldberg, J. B. et al, 1992, Proc. Natl. Acad. Sci. U.S.A. 89(22): 10716-10720 |
| pJHCV32 | Encodes the O7 antigen cluster from *E. coli*, $Tet^R$ | Marolda, C. L., et al., 1999, Microbiology 145 (Pt 9): 2485-95 |
| pJHCV32::Tn3HoHo1-134 | Encodes the O7 antigen cluster from *E. coli* carrying a transposon in wzz, $Tet^R$ $Amp^R$ | |
| pJHCV32::Tn3HoHo1-136 | Encodes the O7 antigen cluster from *E. coli* carrying a transposon in wzy, $Tet^R$ $Amp^R$ | |
| pCW27 | pglK in pMLBAD/Myc-6xHis, $Tp^R$ | Alaimo, C., et al., supra |
| pWA2 | Soluble periplasmic hexa-His-tagged AcrA under control of Tet promoter, in pBR322, $Amp^R$ | Feldman, M. F., et al., supra |
| pMAF10 | HA-tagged PglB cloned in pMLBAD, $Tp^R$ | Feldman, M. F., et al., supra |

TABLE 1-continued

| Strain | Description | Source/Reference |
| --- | --- | --- |
| pPR1347 | Encodes the O antigen cluster of *Salmonella enterica* LT2 | Neal BL, Brown PK, Reeves PR. 1993, *J. Bacteriol.* 175(21): 7115-8. |
| pAMF3 | PilE cloned in pEXT20, Amp$^R$ | Faridmoayer, A. et al., supra |
| pAMF4 | His$_{10}$-tagged PglL cloned in pSPORT1, Km$^R$ | |
| pAMF5 | His$_{10}$-tagged PglL cloned in pEXT22, Km$^R$ | |
| pAMF6 | PilE cloned in pEXT21, Sp$^R$ | |
| pAMF7 | His$_6$-tagged PilE cloned in pEXT20, Amp$^R$ | |
| pAMF8 | PglL cloned in pEXT20, Amp$^R$ | |
| PAMF9 | His$_6$-tagged PilE cloned in pMLBAD Tp$^R$ | |
| PAMF14 | His$_6$-tagged PilE cloned in pEXT21, Sp$^R$ | |
| pPilES63A | PilE mutated at Ser 63 to Ala, cloned in pEXT21, Sp$^R$ | |
| pPilET62A | PilE mutated at Thr 63 to Ala, cloned in pEXT21, Sp$^R$ | |
| pPilEN61A | PilE mutated at Asn 61 to Ala, cloned in pEXT21, Sp$^R$ | |
| pPilEN60A | PilE mutated at Asn 60 to Ala, cloned in pEXT21, Sp$^R$ | |

Cloning and Expression of pilE, and pglL of *N. meningitidis* MC58

The pilE gene (Accession No. AAF40497) was amplified from the genomic DNA of *N. meningitidis* MC58 using pfu DNA polymerase and oligonucleotides, PilEEcoRI (AAA-GAATTCATGAACACCCTTCAAAAAG-GTTTTACCCTTATCGAGC)(SEQ ID NO: 1) and PilEHin-dIII (TTTAAGCTTTTAGCTGGCATCACT-TGCGTCGCGGCAGGTTGACG) (SEQ ID NO: 2). The PCR product was cut with EcoRI and HindIII and cloned into same sites of pEXT20 and pEXT21 to construct pAMF3 and pAMF6, respectively.

The pglL gene (Accession No. AAF41024) was amplified by PCR with oligonucleotides PglLEcoRI(AAAGAAT-TCATGCCCGCTGAAACGACCGTATCCGGCGCGC) (SEQ ID NO: 3) and PglLHindIII-His (TTTAAGCTTTCAGTGGTGGTGGTG-GTGGTGGTGGTGGTGGTGTTTG-CAGGGTTTTGCTTCCGGATGACCGGGC)(SEQ ID NO: 4) using Vent DNA polymerase (New England Bio Labs,) with *N. meningitidis* MC58 as template. PglLHindIII-His encodes a 10×His at the C-terminus. The PCR product was cut with EcoRI and HindIII and inserted into the same site of pSPORT1 to produce pAMF4. pAMF4 was cut with EcoRI and HindHII and the fragment containing the pglL gene was ligated into the same sites of pEXT22 to create pAMF5. pilE-6Ris was amplified using pAMF3 as the template using Pfu DNA polymerase and oligonucleotide PilEEcoRI and PilES all-His (AATCCAGTCGACTTAGTGGTGGTG-GTGGTGGTGGCTGGCATCACT-TGCGTCGCGGCAGGTTGACG)(SEQ ID NO: 5). The PCR product was cut with EcoRI and SalI inserted into the same sites of pEXT20 and pEXT21 to construct pAMF7 and pAMF14. pAMF8 was constructed as follows: pglL was amplified with pAMF4 as the template using Pfu DNA polymerase and oligonucleotide PglLEcoRI and PglLSalI (AATCCAGTCGACTCATTTG-CAGGGTTTTGCTTCCGGATGACCGGGC)(SEQ ID NO: 6). The PCR product was cut with EcoRI and SalI inserted into the same sites of pEXT20 to construct pAMF8. The insert of pAMF7 cut with EcoRI and HindIII and inserted into the same site of pMLBAD to produce pAMF9, expressing His6-tagged PilE.

Western Blot Analysis

Western blots were carried out using techniques known in the art. The presence of proteins on nitrocellulose membranes was detected with antibodies and/or lectins. Table 2 provides information about antibodies and lectins used in this study. Of course, one of skill in the art will appreciate that different antibodies and lectins not contained within Table 2 may also be used.

Soybean agglutinin (SBA) lectin blotting was used to detect glycosylated pilin with *Campylobacter* glycan. Proteins were transformed onto a nitrocellulose membrane and blocked with 5% bovine serum albumin (BSA) in phosphate buffer saline containing 0.1% Tween (PBST) for 1 hr at room temperature. The blocked membrane was incubated for 1 hr at room temperature with biotin-conjugated SBA and washed prior to incubation for another hour with anti-biotin conjugated with horseradish peroxidase. The blot was developed using the ECL kit (GEAmersham). Lipopolysaccharide (LPS) constituted of O7 antigen subunits was detected by STL3, an L-rhamnose-binding isolectin (Tateno, H. et al., 2001, Biosci. Biotechnol. Biochem. 65(6):1328-38). *E. coli* Sϕ874 cells expressing different variants of O7 LPS were mixed with Laemmli buffer and proteins were digested by proteinase K (Roche). LPS were transformed onto nitrocellulose membrane, blocked with BSA, and incubated with STL3. The membrane was incubated with anti-STL3 polyclonal antibody and anti-rabbit for 1 hr at room temperature, respectively. The blot was developed as described before.

TABLE 2

| Antibodies | Description | Dilution | Source |
| --- | --- | --- | --- |
| α-pilin | Polyclonal antibody against *P. aeruginosa* 1244 pilin (rabbit) | 1:2,000 | Comer, J. E. et al., 2002, *Infect. Immun.* 70: 2837-45 |

TABLE 2-continued

| | | | |
|---|---|---|---|
| α-pilin (SM1) | Monoclonal antibody against Nm pilin (mouse) | 1:500 | Virji, M. et al., 1989, *J. Gen. Microbiol.* 135: 3239-51 |
| R12 | *Campylobacter* glycan specific polyclonal antibody (rabbit) | 1:1,000 | Kowarik, M. et al., 2006, *Embo J.* 25: 1957-66 |
| α-O11 | *P. aeruginosa* O11 serogroup glycan specific monoclonal antibody (mouse) | 1:500 | Rougier Bio-Tech Ltd., Montreal, Quebec, Canada |
| α-His tag | A-6xHis epitope tag polyclonal antibody, peroxidise conjugate | 1:2,000 | Rockland |
| Goat α-Mouse IgG | Peroxidase conjugated | 1:8,000 | Rockland |
| Goat α-Mouse IgM | Peroxidase conjugated | 1:10,000 | Calbiochem |
| Goat α-biotin | Peroxidase conjugated | 1:5,000 | Sigma |
| Goat α-rabbit | Peroxidase conjugated | 1:8,000 | Bio-Rad |
| α-STL3 | Polyclonal antibody against STL3 lectin | 1:6,000 | Tateno, H., et al., 1998, *J. Biol. Chem.*, 273: 19190-7 |

| Lectins | Sugar specificity | Concentration | |
|---|---|---|---|
| STL3 | Rhamnose-binding lectin | 2.5 µg/ml | Tateno, H., et al., supra |
| SBA | GalNAc-binding lectin, biotin conjugated | 2.5 µg/ml | Vector Labs |

Purification of Glycosylated Pilin Using Affinity Chromatography

Pilin from the MC58 strain (encoded by the pilE gene), glycosylated with the *C. jejuni* glycan was produced in *E. coli* SCM3 transformed with pAMF5, pAMF14 (expressing C-terminal 6× His tagged pilE, table I), and pACYCpglB$_{mut}$. IPTG (0.5 mM) was added to the cultures and cells were harvested at stationary phase. Pellets were washed with 30 mM Tris-HCl buffer (pH 8.0) containing 0.3 M NaCl (buffer 1) and resuspended in the same buffer containing Complete EDTA-free, protease inhibitor cocktail (Roche). Cells were disrupted by French press and centrifuged at 10,000×g for 10 min to remove cell debris. Membranes were separated by ultracentrifugation (200,000×g for 2 h) and resuspended in buffer 1 containing 2% n-dodecyl-β-D-maltoside (DDM), (buffer 2). The suspension was centrifuged (200,000×g for 1 h) and then imidazole added to the supernatant at the final concentration of 20 mM. The solution was applied to Ni—NTA agarose column (Qiagen) previously equilibrated with buffer 2 containing 20 mM imidazole and washed with the same buffer to remove unbound proteins. The bound proteins were eluted from the column using buffer 2 containing 250 mM imidazole. The eluate was dialyzed overnight at 4° C. in 50 mM Tris-HCl, pH 8.5, containing 10 mM NaCl, 1 mM DTT, and 0.8% DDM (buffer 3). Protein solutions were applied to SBA-agarose column (Vector Labs) equilibrated by buffer 3. Unbound proteins were removed by washing column with buffer 3 and proteins were eluted with buffer 3 containing 0.5 M D-galactose. Protein fractions were collected and kept at −20° C.

β-Elimination of O-glycans

An *E. coli* CLM24 strain producing O-glycosylated PilE was used in this experiment. This strain was transformed with pAMF5, pAMF6 and pACYCpglBmut. The whole cells were harvested and mixed with Laemmli sample buffer (4% SDS, 20% glycerol, 10% 2-mercaptoethanol, 0.004% bromophenol blue and 0.125 M Tris-HCl, pH 6.8) and heated for 10 minutes at 95° C. The samples were fractionated by SDS-PAGE in 10% gels. Proteins were transferred to polyvinylidene fluoride (PVDF) membrane and cut into strips. Membrane strips were treated with different concentrations of sodium hydroxide (0.055, 0.07, 0.09 M). The effect of alkali treatment on the deglycosylation of proteins (i.e., β-elimination) was detected after 16 hrs incubation at 40° C. using the R12 glycan-specific antibody.

In order that the invention be more fully understood, the following examples are set forth. These examples are for illustrative purposes only and are not to be construed as limiting the scope of the invention in any way. Moreover, these examples are not intended to exclude equivalents and variations of the present invention, which are apparent to one skilled in the art.

EXAMPLE 1

Functional Expression of PglL in *E. coli*

Mutagenesis of pglL in *N. meningitidis* resulted in the production of unglycosylated pilin. PglL in *E. coli* was expressed and analyzed with respect to the glycosylation of *N. meningitidis* pilin, which is encoded by the pilE gene. Plasmids pACYCpglB$_{mut}$ and pAMF3, expressing the *N. meningitidis* pilin gene pilE, were transformed into CLM24 cells. The plasmid pACYCpgl carries the pgl locus, encoding all of the enzymes needed for the synthesis of the glycan normally transferred during N-glycosylation in *C. jejuni* (FIG. 1A) (4). Its derivative pACYCpglB$_{mut}$ carries a mutation inactivating the PglB oligosaccharyltransferase. Two bands, presumably corresponding to pre-mature and mature pilin were detected in whole cell extracts by western blot analysis using a monoclonal antibody directed against *N. meningitidis* pilin (see upper panel of FIG. 2A). When these cells were additionally transformed with plasmid pAMF5, which encodes PglL, an extra band of slower electrophoretic mobility was detected with both a monoclonal anti-pilin antiserum and the *C. jejuni* glycan-specific R12 antiserum (see FIG. 2A, lanes 3), indicating that pilin was glycosylated. As the presence of glycosylated pilin was PglL-dependent, it was concluded that PglL possesses OTase activity. The structure of the *C. jejuni* glycan transferred in this experiment by PglL is different than the trisaccharide found in *N. meningitidis* pilin (FIG. 1B), indicating that PglL also has relaxed sugar specificity.

Figure 3:
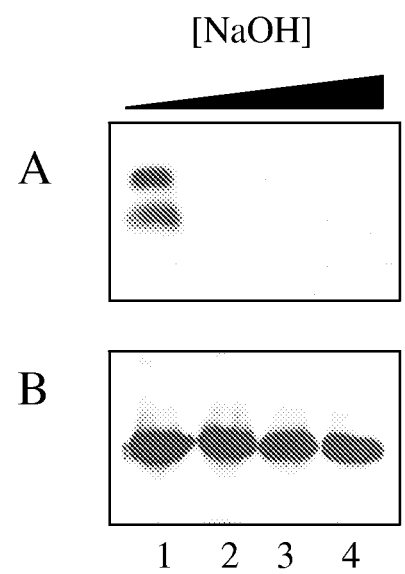
FIG. 3 is western blot analyses showing susceptibility of N. meningitidis (MC) glycosylated pilin to beta elimination. Extracts of E. coli CLM24 cells containing pilin glycosylated with C. jejuni glycan were used in this experiment (FIG. 3A). Extracts of the same strain containing N-glycosylated AcrA with C. jejuni glycan were used as the control (FIG. 3B). The whole cells were harvested and mixed with Laemmli sample buffer (4% SDS, 20% glycerol, 10% 2-mercaptoethanol, 0.004% bromophenol blue and 0.125 M Tris-HCl, pH 6.8) and heated for 10 min. at 95° C. The samples were fractionated by SDS-PAGE in 15% gels, transferred to polyvinylidene fluoride (PVDF) membrane and cut into strips. The effect of alkali treatment on the deglycosylation of proteins, β-elimination, was detected after 16 hrs incubation at 40° C. using the R12 glycan-specific antibody. Once transferred to PVDF membranes, the samples were treated with different concentrations of sodium hydroxide (NaOH). Lane 1, no treatment with NaOH. Lane 2, treatment with 0.055 M NaOH. Lane 3, treatment with 0.07 M NaOH. Lane 4, treatment with 0.09 M NaOH.

O-linked glycans can be released from proteins by a β-elimination reaction under mild alkaline conditions. On the contrary, N-glycans are not detached from proteins in these conditions. The linkage between pilin and the *C. jejuni* glycan was susceptible to β-elimination (see FIG. 3). Whole cell extracts containing glycosylated pilin were transferred to PVDF membranes and treated with different concentrations of NaOH according to the protocol described by Duk et al (1997, *Anal. Biochem.* 253:98-102). The protein-linked glycan was detected with the R12 antiserum. The linkage between pilin and the glycan was alkali-labile, whereas N-glycosylated AcrA was resistant to the treatment (FIG. 3B), confirming that as expected, pilin was actually O-glycosylated.

Figure 2:
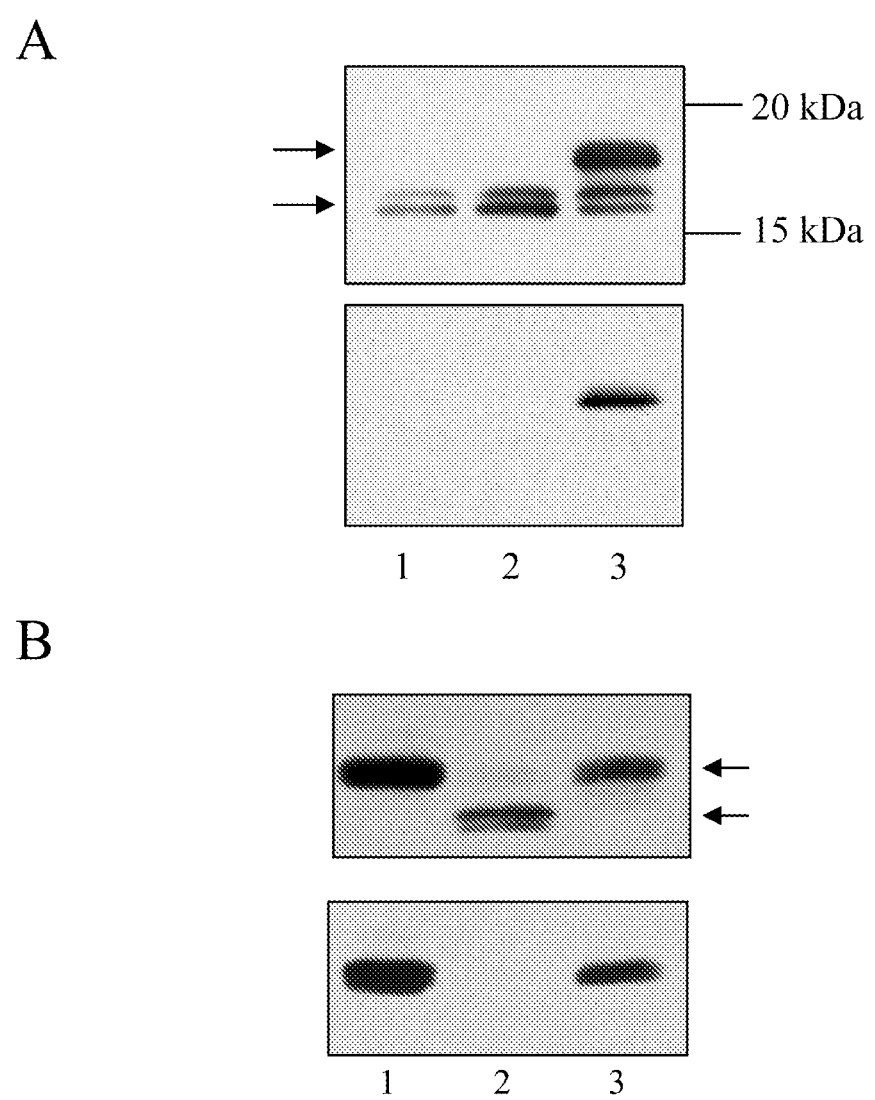
FIG. 2A is a western blot analysis of whole-cell E. coli CLM24 extracts producing unglycosylated and glycosylated N. meningitidis (MC) pilin. Pilin was detected by the SM1 anti-pilin monoclonal antibody (upper panel) or the C. jejuni glycan antiserum R12 (lower panel). R12 is an anti-serum that recognizes specifically the C. jejuni glycan (Wacker, M. et al., 2002, Science 298(5599):1790-1793). Lane 1, pAMF3 (expressing MC pilin) and pAMF5 (expressing PglL). Lane 2, pAMF3, pACYCpglB$_{mut}$ and pEXT22 (cloning vector). Lane 3, pAMF3 (expressing MC pilin), pACYCpglB$_{mut}$, and pAMF5 (expressing PglL). The plasmid pACYCpgl carries the pgl locus, encoding all of the enzymes needed for the synthesis of the glycan normally transferred during N-glycosylation in C. jejuni (FIG. 1A) (Wacker, M. et al., supra). Its derivative pACYCpglB$_{mut}$ carries a mutation inactivating the PglB oligosaccharyltransferase. The upper arrow indicates the glycosylated product, and the lower arrow indicates the unglycosylated products.
FIG. 2B is a western blot analysis showing the effect of mutations S63A and T62A on pilin glycosylation. Pilin was detected by the SM1 anti-pilin monoclonal antibody (upper panel) or the C. jejuni glycan antiserum R12 (lower panel). All lanes correspond to cells expressing pAMF5, and pACYCpglB$_{mut}$. Lane 1, pPilET62A. Lane 2, pPilES63A. Lane 3, pAMF6. The upper arrow indicates the glycosylated product, and the lower arrow indicates the unglycosylated products.
Figure 4:
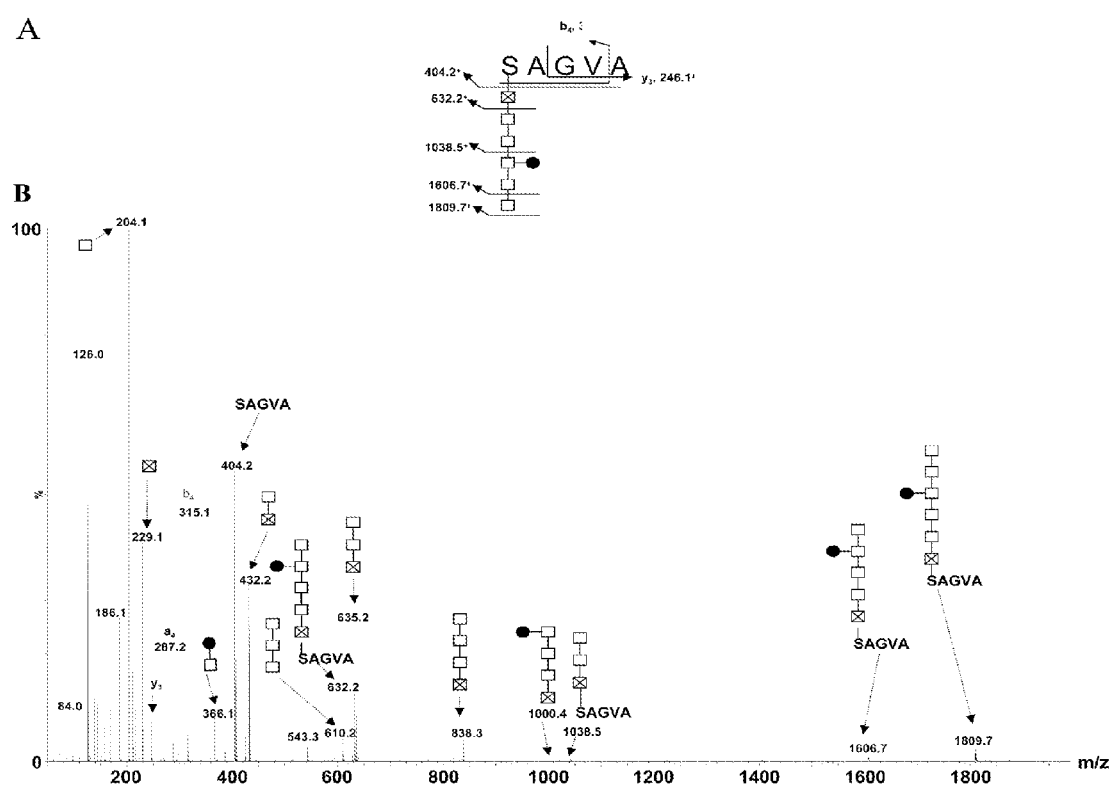
FIG. 4A is the fragmentation pattern expected from proteinase K digestion of glycosylated MC pilin. Crossed squares represent DATDH (2,4-diacetamido-2,4,6-trideoxyhexose). Open squares represent HexNAc. Filled circles represent Hexose.
FIG. 4B is a MS/MS spectrum of a double charged glycopeptide ion at m/z $905.8^{2+}$ corresponding to DATDH(HexNAc)5Hex attached to peptide $^{63}$SAGVA$^{67}$, resulting from proteinase K digestion of MC pilin. The common peptide fragment ions ($y_3$ and $b_4$) shown in FIG. 4A are observed, in addition to the sugar fragments and the peptide with sugar fragments. Crossed squares represent DATDH (2,4-diacetamido-2,4,6-trideoxyhexose). Open squares represent HexNAc. Filled circles represent Hexose.

This is further supported by the fact that mutation of S63 abolished glycosylation (FIG. 2B, lanes 2). Further support of O-glycosylation is provided by the observation that the pentapeptide $S^{63}AGVA^{67}$ (SEQ ID NO: 7) was attached to a *C. jejuni* glycan, as identified by mass spectrometry (FIG. 4).

EXAMPLE 2

PglL can Transfer a Polysaccharide, Whereas pilO Transfers Only Short Carbohydrates.

Figure 5:
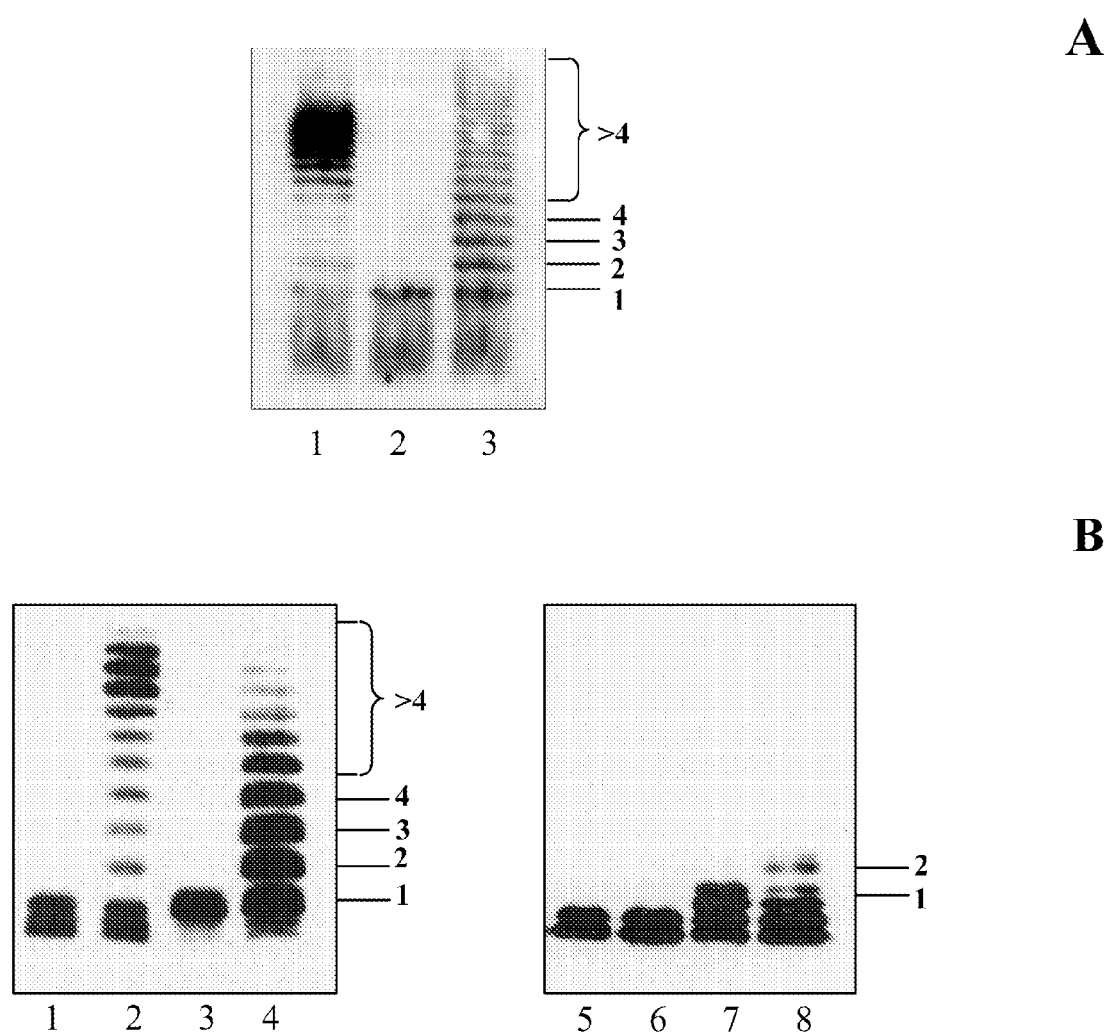
FIG. 5A is a lectin blot analysis of three different forms of E. coli O7 LPS produced in E. coli SΦ874. A lectin specific for rhamnose, which is one of the sugars of the O7 antigen, has been used. Lane 1, wild-type. Lane 2, wzy (polymerase) mutant. Lane 3, wzz (chain length regulator) mutant. The numbers at the right indicate the number of O7 repeating units attached to the lipid A-core.
FIG. 5B is a western blot analysis demonstrating the ability of PglL (left panel) and PilO (right panel) to transfer O7 antigen of different lengths to their respective pilins in the E. coli SCM3 strain (ligase-deficient derivative of SΦ874). N. meningitidis (MC) pilins containing the three O antigen versions shown in FIG. 5A were detected using the anti-MC pilin monoclonal antibody. PglL was able to transfer fully polymerized O7 antigen to MC pilin (lane 2). P. aeruginosa pilin containing O antigen of only up to two repeating units was detected in the wzz mutant strain (lane 8), despite the observation that O antigen containing two and more repeating units are equally abundant (see FIG. 5A, lane 3). Lanes 1-4: pAMF5 (expressing PglL) and pAMF6 (expressing MC pilin). Additionally, lane 2 contains pJHCV32 (wild-type O7 antigen), lane 3 contains pJHCV32-134 (O7 wzy mutant), and lane 4 contains pJHCV32-136 (O7 wzz mutant). Lanes 5-8, pPAC46 (expressing P. aeruginosa pilin and PilO). Additionally, lane 6 contains pJHCV32, lane 7 contains pJHCV32-134, and lane 8 contains pJHCV32-136.

O-antigen polymerization and, as we have shown, pilin glycosylation both occur at the bacterial periplasm. The transfer of polymerized O7 antigen (FIG. 1C) by PilO in *E. coli* was tested. The SΦ874 strain (Table 1) carries a deletion encompassing the complete endogenous O-antigen cluster. To generate O-linked polysaccharides, plasmids containing the gene cluster necessary for the synthesis of the *E. coli* O7 antigen in the SΦ874 strain were introduced. Three different O7 antigen variants were produced using different plasmids: wild-type O7 antigen (O7 WT; see lane 1 in FIG. 5A); an O antigen polymerase (O7wzy$_{mut}$) mutant that only produces a single O7 subunit (see lane 2 in FIG. 5A); and a mutant in O-chain length regulator (OT wzz$_{mut}$) gene that produces an O antigen with altered length distribution (see lane 3 in FIG. 5A) (20). The ability of PilO to transfer the three variants of the O7 antigen in the SCM3 strain (Table 1), a derivative of the SΦ874 strain lacking the waaL gene, was observed. In the wzy mutant, a single subunit of O7 antigen was transferred to pilin (FIG. 5B, lane 7). Although transfer of O7 antigen in the wild-type O7 antigen was undetectable (FIG. 5B, lane 6), up to two O antigen subunits were transferred to pilin in the wzz mutant (FIG. 5B, lane 8). O antigen chains containing three or more repetitive subunits were not transferred to pilin, although the wzz mutant produces similar quantities of chains containing two, three and four O repeating units (FIG. 5A, lane 3). Therefore, PilO cannot transfer O antigen glycans containing more than two repetitive subunits. Glycosylated pilin was not detected in the wild-type O7 strain because the formation for the short chains that transferable by PilO are reduced by Wzz activity. On the contrary, PglL was able to transfer short and also fully polymerized O7 antigen (FIG. 5B, lanes 5-8).

Figure 6:
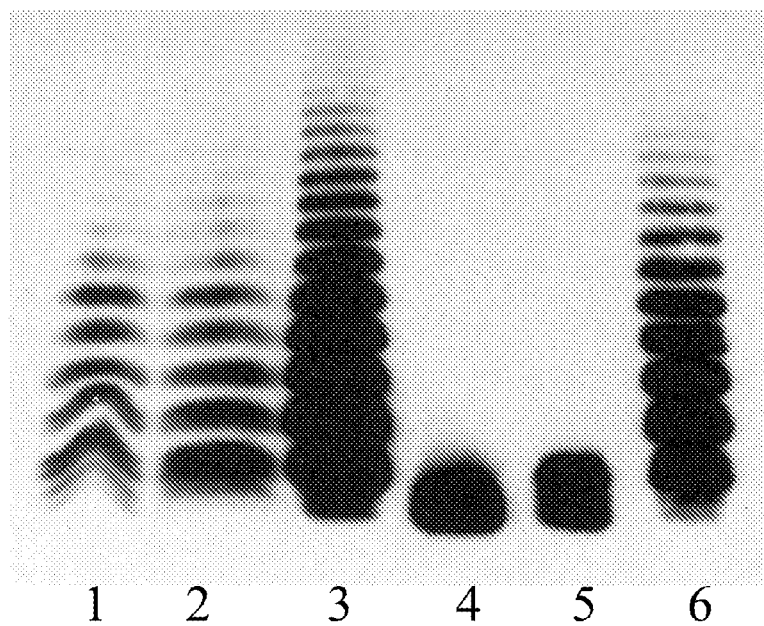
FIG. 6 is a western blot analysis showing that mutation of serine 63 abolishes glycosylation. O7 antigen from the wzz mutant strain is not transferred to the S63A variant of MC pilin (lane 4). Glycosylation is not affected in the mutants N60A (lane 1), N61A (lane 2), and T62A (lane 3). Unglycosylated (lane 5) and wild-type pilin glycosylated with the O7 antigen (lane 6) are included for comparison. Lanes 1-4 contain plasmid pAMF5 and pJHCV32::Tn3HoHo1-134. Lane 1, pPilEN60A. Lane 2, pPilEN61A. Lane 3, pPilET62A. Lane 4, pPilES63A. Lane 5, pAMF6, pEXT21 and pJHCV32::Tn3HoHo1-134. Lane 6, pAMF6, pAMF5 and pJHCV32: :Tn3HoHo1-134.

FIG. 6 shows that the polysaccharide is transferred to a serine residue, since mutation of N60, N61 and T62 do not affect glycosylation, whereas mutation S63A completely abolishes transfer of the polysaccharide to PilE.

EXAMPLE 3

Figure 7:
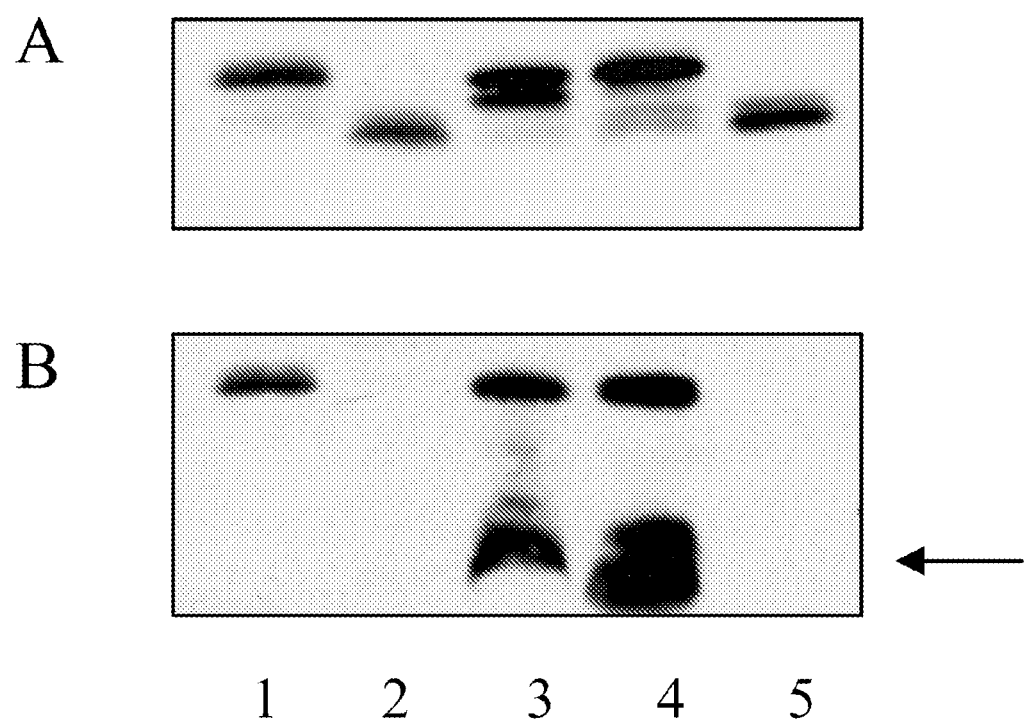
FIGS. 7A and 7B are western blot analyses showing that glycosylation of MC pilin only occurs in the presence of a functional flippase, either Wzx (lane 1), a pgl-encoded PglK (lane 3) or a PglK encoded in trans (lane 4). Cell extracts were analyzed by western blot using antibodies directed against MC pilin (FIG. 7A) and the glycan-specific R12 antiserum (FIG. 7B). Lanes: 1, CLM24 strain containing pAMF5, pAMF6 and pACYCpglB$_{mut}$. Lane 2, SCM7 transformed with plasmids pAMF5, pAMF6 and pACYCpglK$_{mut}$. Lane 3, SCM7 containing pAMF5, pAMF6 and pACYCpgl. Lane 4, SCM7 transformed with pAMF5, pAMF6, pACYCpglK$_{mut}$, and pCW27, expressing PglK in trans. Lane 5, SCM7 transformed with pAMF5, pAMF6, pACYCpglK$_{mut}$ and pMLBAD (cloning vector). Details of the strains and plasmids are presented in Table 1. The arrow indicates the presence of LPS containing the *C. jejuni* oligosaccharide in the strains where a functional WaaL (ligase) and a flippase are present.

Translocation of Und-PP-glycan to the Periplasm is Required for PilO and PglL Activity In O-antigen, peptidoglycan, exopolysaccharides and capsule biosynthesis, as well as in protein N-glycosylation in *C. jejuni*, undecaprenol-pyrophosphate (Und-PP) substrates are translocated or "flipped" into the periplasm by the action of flippases (Alaimo, C., et al., supra). The *E. coli* SCM7 strain lacks all the known flippases, and it has been recently used to characterize PglK, the flippase of the *C. jejuni* glycosylation system (Table 1) (Alaimo, C., et al., supra). This strain was used to identify the cell compartment where pilin glycosylation takes place. pPAC46 and pACYCpgl or pACYCpglK (Table 1) were introduced in SCM7 cells. Pilin glycosylation was detected in the cells carrying the intact pgl cluster. pACYCpglK carries a non-polar mutation in the pglK gene. Pilin was not glycosylated in SCM7 cells carrying pACYCpglK, where no flippase was present and therefore translocation of Und-PP-glycans into the periplasm is impeded (see lane 2, FIGS. 7A and 7B). PglL activity was detected only in the presence of a functional flippase in the cells. Thus, translocation of the Und-PP-linked oligosaccharide is required for PglL-dependent glycosylation, indicating that PglL activities are localized to the periplasm.

EXAMPLE 4

PglL can Transfer Glycans Carrying a Hexose at the Reducing End to the Pilin

Figure 8:
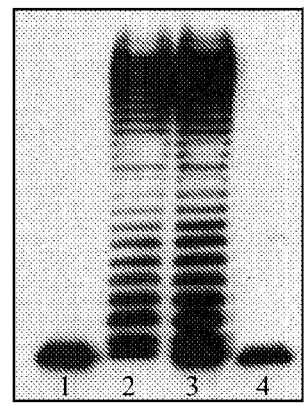
FIG. 8A is a western blot analysis using anti-pilin in *E. coli* JM109 cells expressing *Salmonella* O-antigen. This blot shows that the pilin can be glycosylated with a polysaccharide having galactose at the reducing end in *E. coli*. Lanes 1 to 3 contain pPR1347 and pAMF8. In addition, lane 1, pPilES63A. Lane 2, pAMF9. Lane 3, pPilET62A. Lane 4, pPR1347, pAMF9, and pEXT20.
FIG. 8B is a reconstitution of pilin glycosylation in *Salmonella*. Left panel, *Salmonella enterica* serovar *Typhimurium*, strain SL3749 transformed with pAMF9. Lane 1, pEXT20. Lane 2, pAMF8. This panel shows the transfer of a polysaccharide in *Salmonella* cells. Middle panel, *Salmonella enterica Typhimurium*, strain SL901 carrying a mutation in the wzy polymerase gene, transformed with pAMF9 (in both lanes 3 and 4). Lane 3 contains pEXT20. Lane 4 contains pAMF8. Right panel, *Salmonella enterica* serovar *Typhi*, carrying a mutation in the wzy polymerase gene, transformed with pAMF9. Lane 5, pEXT20. Lane 6, pAMF8. The middle and right panels demonstrate the transfer of oligosaccharides into different *Salmonella* strains.
Figure 8:
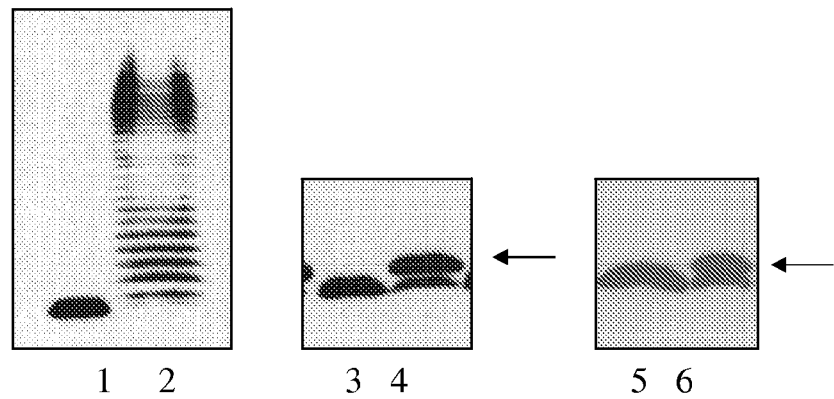

*Salmonella enterica* O-antigen from different serovars (i.e., *Typhimurium* and *Typhi*) are composed of repeating subunits with a hexose at the reducing end (FIG. 1). To test if PglL can transfer a glycan containing a hexose at the reducing end, PglL and PilE were co-expressed in *E. coli* JM109 carrying plasmid pPR1347 (Table 1), which encodes the enzymes required for the synthesis of *S. enterica* serovar *Typhimurium* O antigen. Western blot analysis using anti-pilin showed this O antigen can be transferred to PilE by PglL in *E. coli* (see FIG. 8A, lane 2). Replacing PglL with the corresponding empty vector resulted in expression of the unglycosylated pilin (FIG. 8A, lane 4). In addition, the pilin mutant T62A is also glycosylated with *Salmonella* O antigen (FIG. 8A, lane 3) while pilin mutant S63A abolishes glycosylation (FIG. 8A, lane 1). This demonstrates that a glycan containing galactose at the reducing end can be attached to a serine residue in PilE.

Furthermore, glycosylation of pilin can be accomplished in the original host *S. enterica* when both PglL and PilE are present (FIG. 8B, lane 2). Replacing the plasmid encoding PglL with the corresponding empty vector resulted in unglycosylated pilin (FIG. 8B, lane 1). PglL can also transfer a single subunit of O antigen produced in the Wzy mutants of *S. enterica* serovar *Typhimurium* (FIG. 8B, lane 4), and in the Wzy mutants of *S. enterica* serovar *Typhi* (FIG. 8B, lane 6). Arrows in FIG. 8B indicate the position of glycosylated pilin with a single O antigen subunit. Lanes 3 and 5 are negative controls of glycosylation, in which the plasmid expressing PglL has been replaced by the corresponding empty vector.

What is claimed is:

1. A method for O-glycosylating heterologous proteins with a polysaccharide of more than 10 monosaccharides in a bacterial host cell, the method comprising introducing into the bacterial host cell, in any particular order, at least:
   (a) DNA comprising a gene that produces a PglL oligosaccharyltransferase; and
   (b) DNA comprising a gene that produces a heterologous protein to be O-glycosylated with the polysaccharide;
wherein the PglL oligosaccharyltransferase facilitates the covalent attachment of the polysaccharide to the heterologous protein to produce the O-glycosylated heterologous protein.

2. The method of claim 1, wherein the method further comprises introducing DNA comprising a gene required for the assembly of the polysaccharide onto a lipid carrier.

3. The method of claim 1, wherein the PglL oligosaccharyltransferase is derived by a protein expressed by pglL of *Neisseria*.

4. The method of claim 1, wherein the gene that produces a protein to be O-glycosylated comprises pilE from *Neisseria*.

5. The method of claim 1, wherein the gene that produces the PglL oligosaccharyltransferase is pglL and the gene that produces the protein to be O-glycosylated is pilE.

6. The method of claim 1, wherein the bacterial host cell is *Escherichia coli*.

7. The method of claim 1, wherein the bacterial host cell is *Salmonella*.

8. The method of claim 1, wherein the polysaccharide comprises a hexose or an N-acetyl hexose derivative at the reducing end.

9. The method of claim 2, wherein the lipid carrier is a polyprenol-pyrophosphate comprising undecaprenol-pyrophosphate, dolichol-pyrophosphate, or synthetic equivalent thereof.

10. The method of claim 2, wherein the gene comprises a glycosyl transferase or an enzyme required for assembly and transport of the polysaccharide.

11. A method for producing O-glycosylating heterologous proteins with a polysaccharide of more than 10 monosaccharides in a bacterial host cell, the method comprising introducing into the bacterial host cell, in any particular order, at least:
   (a) DNA comprising pglL that produces a PglL oligosaccharyltransferase;
   (b) DNA comprising pilE that produces a heterologous protein to be O-glycosylated with the polysaccharide; and
   (c) DNA comprising a gene required for the assembly of a glycan onto a lipid carrier,
wherein the PglL oligosaccharyltransferase facilitates the covalent attachment of the polysaccharide to the heterologous protein to produce the O-glycosylated heterologous proteins.

12. The method of claim 11, wherein the DNA comprising pglL is pglL of *Neisseria*.

13. The method of claim 11, wherein the DNA comprising pilE is pilE from *Neisseria*.

14. The method of claim 11, wherein the bacterial host cell is *Escherichia coli*.

15. The method of claim 11, wherein the bacterial host cell is *Salmonella*.

16. The method of claim 11, wherein the polysaccharide comprises a hexose or an N-acetyl hexose derivative at the reducing end.

17. The method of claim 12, wherein the lipid carrier is a polyprenol-pyrophosphate comprising undecaprenol-pyrophosphate, dolichol-pyrophosphate, or synthetic equivalent thereof.

18. The method of claim 11, wherein the gene comprises a glycosyl transferase or an enzyme required for assembly and transport of the polysaccharide.

19. A vaccine comprising an O-glycosylated protein produced by the method of claim 1.

20. A pharmaceutical composition comprising an O-glycosylated protein produced by the method of claim 1.

21. A method for O-glycosylating heterologous proteins with a glycan in a bacterial host cell, the method comprising introducing into the bacterial host cell, in any particular order, at least:
   (a) DNA comprising a gene that produces a PglL oligosaccharyltransferase; and
   (b) DNA comprising a gene that produces a heterologous protein to be O-glycosylated with the glycan;
wherein the PglL oligosaccharyltransferase facilitates the covalent attachment of the glycan to an internal glycosylation site in the heterologous protein to produce the O-glycosylated heterologous protein.

22. The method of claim 21, wherein the method further comprises introducing DNA comprising a gene required for the assembly of the glycan onto a lipid carrier.

23. The method of claim 21, wherein the PglL oligosaccharyltransferase is derived by a protein expressed by pglL of *Neisseria*.

24. The method of claim 21, wherein the gene that produces a protein to be O-glycosylated comprises pilE from *Neisseria*.

25. The method of claim 21, wherein the gene that produces the PglL oligosaccharyltransferase is pglL and the gene that produces the protein to be O-glycosylated is pilE.

26. The method of claim 21, wherein the bacterial host cell is *Escherichia coli*.

27. The method of claim 21, wherein the bacterial host cell is *Salmonella*.

28. The method of claim 21, wherein the glycan is a polysaccharide of more than 10 monosaccharides.

29. The method of claim 21, wherein the glycan comprises a hexose or an N-acetyl hexose derivative at the reducing end.

30. The method of claim 22, wherein the lipid carrier is a polyprenol-pyrophosphate comprising undecaprenol-pyrophosphate, dolichol-pyrophosphate, or synthetic equivalent thereof.

31. The method of claim 22, wherein the gene comprises a glycosyl transferase or an enzyme required for assembly and transport of the glycan.

32. A method for producing O-glycosylating heterologous proteins with a glycan in a bacterial host cell, the method comprising introducing into the bacterial host cell, in any particular order, at least:
   (a) DNA comprising pglL that produces a PglL oligosaccharyltransferase;
   (b) DNA comprising pilE that produces a heterologous protein to be O-glycosylated with the glycan; and
   (c) DNA comprising a gene required for the assembly of a glycan onto a lipid carrier,
wherein the PglL oligosaccharyltransferase facilitates the covalent attachment of the glycan to an internal glycosylation site in the heterologous protein to produce the O-glycosylated heterologous proteins.

33. The method of claim 32, wherein the DNA comprising pglL is pglL of *Neisseria*.

34. The method of claim 32, wherein the DNA comprising pilE is pilE from *Neisseria*.

35. The method of claim 32, wherein the bacterial host cell is *Escherichia coli*.

36. The method of claim 32, wherein the bacterial host cell is *Salmonella*.

37. The method of claim 32, wherein the glycan is a polysaccharide of more than 10 monosaccharides.

38. The method of claim 32, wherein the glycan comprises a hexose or an N-acetyl hexose derivative at the reducing end.

39. The method of claim 32, wherein the lipid carrier is a polyprenol-pyrophosphate comprising undecaprenol-pyrophosphate, dolichol-pyrophosphate, or synthetic equivalent thereof.

40. The method of claim 32, wherein the gene comprises a glycosyl transferase or an enzyme required for assembly and transport of the glycan.

41. A vaccine comprising an O-glycosylated protein produced by the method of claim 21.

42. A pharmaceutical composition comprising an O-glycosylated protein produced by the method of claim 21.

43. A method for O-glycosylating heterologous proteins with a glycan in a bacterial host cell, the method comprising introducing into the bacterial host cell, in any particular order, at least:
 (a) DNA comprising a gene that produces a PglL oligosaccharyltransferase; and
 (b) DNA comprising a gene that produces a heterologous protein to be O-glycosylated with the glycan;
wherein the PglL oligosaccharyltransferase facilitates the covalent attachment of the glycan to the heterologous protein to produce the O-glycosylated heterologous protein, and wherein the glycan comprises a hexose or an N-acetyl hexose derivative at its reducing end.

44. The method of claim 43, wherein the method further comprises introducing DNA comprising a gene required for the assembly of the glycan onto a lipid carrier.

45. The method of claim 43, wherein the PglL oligosaccharyltransferase is derived by a protein expressed by pglL of *Neisseria*.

46. The method of claim 43, wherein the gene that produces a protein to be O-glycosylated comprises pilE from *Neisseria*.

47. The method of claim 43, wherein the gene that produces the PglL oligosaccharyltransferase is pglL and the gene that produces the protein to be O-glycosylated is pilE.

48. The method of claim 43, wherein the bacterial host cell is *Escherichia coli*.

49. The method of claim 43, wherein the bacterial host cell is *Salmonella*.

50. The method of claim 43, wherein the glycan is a polysaccharide of more than 10 monosaccharides.

51. The method of claim 43, wherein the covalent attachment comprises an internal glycosylation site.

52. The method of claim 44, wherein the lipid carrier is a polyprenol-pyrophosphate comprising undecaprenol-pyrophosphate, dolichol-pyrophosphate, or synthetic equivalent thereof.

53. The method of claim 44, wherein the gene comprises a glycosyl transferase or an enzyme required for assembly and transport of the glycan.

54. A method for producing O-glycosylating heterologous proteins with a glycan in a bacterial host cell, the method comprising introducing into the bacterial host cell, in any particular order, at least:
 (a) DNA comprising pglL that produces a PglL oligosaccharyltransferase;
 (b) DNA comprising pilE that produces a heterologous protein to be O-glycosylated with the glycan; and
 (c) DNA comprising a gene required for the assembly of a glycan onto a lipid carrier,
wherein the PglL oligosaccharyltransferase facilitates the covalent attachment of the glycan to the heterologous protein to produce the O-glycosylated heterologous proteins, and wherein the glycan comprises a hexose or an N-acetyl hexose derivative at its reducing end.

55. The method of claim 54, wherein the DNA comprising pglL is pglL of *Neisseria*.

56. The method of claim 54, wherein the DNA comprising pilE is pilE from *Neisseria*.

57. The method of claim 54, wherein the bacterial host cell is *Escherichia coli*.

58. The method of claim 54, wherein the bacterial host cell is *Salmonella*.

59. The method of claim 54, wherein the glycan is a polysaccharide of more than 10 monosaccharides.

60. The method of claim 54, wherein the covalent attachment comprises an internal glycosylation site.

61. The method of claim 54, wherein the lipid carrier is a polyprenol-pyrophosphate comprising undecaprenol-pyrophosphate, dolichol-pyrophosphate, or synthetic equivalent thereof.

62. The method of claim 54, wherein the gene comprises a glycosyl transferase or an enzyme required for assembly and transport of the glycan.

63. A vaccine comprising an O-glycosylated protein produced by the method of claim 43.

64. A pharmaceutical composition comprising an O-glycosylated protein produced by the method of claim 43.

* * * * *

UNITED STATES PATENT AND TRADEMARK OFFICE
CERTIFICATE OF CORRECTION

PATENT NO. : 9,238,830 B2
APPLICATION NO. : 12/519085
DATED : January 19, 2016
INVENTOR(S) : Feldman et al.

Page 1 of 1

It is certified that error appears in the above-identified patent and that said Letters Patent is hereby corrected as shown below:

In the Claims:

Claim 17, line 64, Column 23, replace "The method of claim 12" with --The method of claim 11--

Signed and Sealed this
Ninth Day of August, 2016

Michelle K. Lee
*Director of the United States Patent and Trademark Office*